United States Patent
Davey

(10) Patent No.: US 10,633,359 B2
(45) Date of Patent: Apr. 28, 2020

(54) PREPARATION OF MACROCYCLIC LACTONES

(71) Applicant: Givaudan SA, Vernier (CH)

(72) Inventor: Paul Nicholas Davey, Duebendorf (CH)

(73) Assignee: Givaudan SA, Vernier (CH)

( * ) Notice: Subject to any disclaimer, the term of this patent is extended or adjusted under 35 U.S.C. 154(b) by 28 days.

(21) Appl. No.: 16/077,187

(22) PCT Filed: Mar. 8, 2017

(86) PCT No.: PCT/EP2017/055413
§ 371 (c)(1),
(2) Date: Aug. 10, 2018

(87) PCT Pub. No.: WO2017/153455
PCT Pub. Date: Sep. 14, 2017

(65) Prior Publication Data
US 2019/0047974 A1 Feb. 14, 2019

(30) Foreign Application Priority Data

Mar. 10, 2016 (GB) .................................. 1604110.5

(51) Int. Cl.
*C07C 69/533* (2006.01)
*C07D 313/00* (2006.01)
*C08G 61/12* (2006.01)

(52) U.S. Cl.
CPC .......... *C07D 313/00* (2013.01); *C07C 69/533* (2013.01); *C08G 61/127* (2013.01); *C08G 2261/11* (2013.01); *C08G 2261/228* (2013.01); *C08G 2261/334* (2013.01)

(58) Field of Classification Search
USPC ........................................ 528/271, 272, 274
See application file for complete search history.

(56) References Cited

U.S. PATENT DOCUMENTS

2015/0299236 A1  10/2015  Rosebrugh et al.

FOREIGN PATENT DOCUMENTS

CN       101417992 A      4/2009
WO    WO 2014/093687 A1   6/2014

OTHER PUBLICATIONS

PCT/EP2017/055413—International Search Report, dated Apr. 24, 2017.
PCT/EP2017/055413—International Written Opinion, dated Apr. 24, 2017.
Kamau, et al.: "Cyclo-depolymerization of olefin-containing polymers to give macrocyclic oligomers by metathesis and the entropically-driven ROMP of the olefin-containing macrocyclic esters", Polymer, Elsevier Science Publishers B.V, GB, vol. 48, No. 23, Sep. 14, 2007, pp. 6808-6822.
GB 1604110.5—Great Britain Search Report, dated Jan. 13, 2017.
J.T. Patton, et al.:"Acyclic Diene Metathesis (ADMET) Polymerization. The Synthesis of Unsaturated Polyesters", Macromolecules vol. 25 No. 15, pp. 3862-3867 American Chemical Society 1992.
Hatice Mutlu, et al.: "Acyclic diene metathesis: a versatile tool for the construction of defined polymer architectures", Chemical Society Reviews 2011, vol. 40, pp. 1404-1445.

*Primary Examiner* — Terressa Boykin
(74) *Attorney, Agent, or Firm* — Curatolo Sidoti Co., LPA; Salvatore A. Sidoti; Floyd Trillis, III

(57) ABSTRACT

A process for preparing a macrocyclic lactone comprising 14 to 17 ring carbon atoms, the process comprising the steps of i) subjecting a reaction mixture comprising an olefin-containing random polyester, formed by metathesis to a cyclo-depolymerization reaction to form the macrocyclic lactone, and ii) concomitant removal of the macrocyclic lactone from the reaction mixture.

18 Claims, No Drawings

PREPARATION OF MACROCYCLIC LACTONES

CROSS REFERENCE TO RELATED APPLICATIONS

This application is a national stage application of International Application No. PCT/EP2017/055413, filed 8 Mar. 2017, which claims priority from Great Britain Patent Application No. 1604110.5, filed 10 Mar. 2016, which applications are incorporated herein by reference.

FIELD OF THE INVENTION

The present invention relates to the synthesis of macrocyclic lactones by the cyclo-depolymerization of olefin-containing polyesters, as well as to monomers and polymers used in the preparation of said macrocyclic lactones.

BACKGROUND OF THE INVENTION

The macrocyclic lactone is an important structural motif in the chemistry of perfumery ingredients. In particular, macrocyclic lactones are valued for the desirable musk odour they can deliver to all manner of consumer products in both fine and technical perfumery.

The odour of musk is perhaps the most universally appreciated olfactive signal in perfumery. Synthetic musks can be divided into three major classes: aromatic nitro musks, polycyclic musks and macrocyclic musks. However, the detection of the nitro- and polycyclic chemical groups in human and environmental samples initiated a public debate on the use of these compounds; and some research suggested that these musk compounds do not break down in the environment and can accumulate in human bodies. As such, macrocyclic musks have increased in importance for perfumers in recent years.

Common macrocyclic musks include AMBRETTOUDE™ including 9-ambrettolide and 7-ambrettolide), NIRVANOUDE™, HABANOLIDE™ COSMONE™, MUSCENONE VELVIONE™, CIVETONE™ and GLOBANONE™

7-ambrettolide naturally occurs in musk ambrette seed oil (M. Kerschbaum, Chem Ber. 1927, 60B, 902) and is a valuable perfume base because of its desirable odour. 9-ambrettolide is likewise a much appreciated perfumery ingredient; it is currently synthesized industrially from aleuritic acid, which in turn is obtained from natural sources.

The availability and quality of naturally-occurring starting materials are, of course, dependent on climatic conditions, as well as socio-economic factors. Furthermore, since starting materials may be extracted from natural sources, sometimes with modest yields, they are available at prices that will, in all likelihood, increasingly render their use uneconomical on an industrial scale. Accordingly, if commercial industrial supplies of macrocyclic musks, such as AMBRETTOLIDE™, are to continue to be available at a reasonable cost, there is a need for more cost-effective industrially-scalable processes for their production, isolation and purification.

SUMMARY OF THE INVENTION

In a first aspect, the present invention relates to a process for preparing and isolating a macrocyclic lactone by the cyclo-depolymerization of an olefin-containing random polyester contained in a reaction mixture comprising the steps of:
  i) depolymerizing the olefin-containing random polyester in a reaction mixture to form fragments capable of intramolecular cyclization;
  ii) the intramolecular cyclization of said fragments to form a desired macrocyclic lactone; and
  iii) concomitant separation of the macrocyclic lactone from the reaction mixture.

In another aspect, the present invention relates to an olefin-containing random polyester useful in the preparation of macrocyclic lactones.

In yet another aspect, the present invention relates to precursor monomers of said olefin-containing random polyesters.

In yet another aspect, the present invention relates to the use of the olefin-containing random polyesters in the formation of a macrocyclic lactone.

DETAILED DESCRIPTION OF THE INVENTION

The term "random", as it is used in relation to the polyester, refers to the arrangement of the monomer units within the polyester, and more specifically the arrangement whereby the monomer units are arranged in a non-predetermined pattern along the polymer chain.

In a particular embodiment of the present invention, the olefin-containing random polyester contains at least one unit of the formula

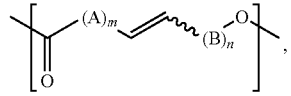

wherein
  A is a divalent radical —CHR—, wherein R is hydrogen or a $C_{1-4}$ alkyl group;
  B is a divalent radical —CHR'—, wherein R' is hydrogen or a $C_{1-4}$ alkyl group;
  the sum of n and m is an integer selected from 11, 12, 13 or 14; and
  wherein the divalent radicals A and B contained in the unit may be the same or different.

In a more particular embodiment of the invention, the olefin-containing random polyester contains at least one each of the following units

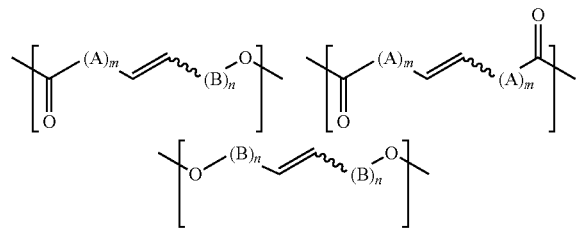

wherein A, B, m and n are as hereinabove defined.

The olefin-containing random polyester of the present invention may be acyclic or cyclic. The polymer chain may contain any number of monomeric units. In particular, the olefin-containing random polyester may consist of a mixture of polymers having a distribution of monomer units between 2 to 100, more particularly 10 to 50, and more particularly still 10 to 25.

The olefin-containing random polyester may be prepared by polymerizing a diene ester monomer using diene metathesis. A suitable monomer is an ester containing a first reactive olefin group located on the alcohol side of the ester (alcoholic olefin), and a second reactive olefin group on the carboxylic side of the ester (carboxylic olefin). It will be apparent to the skilled person that metathesis reactions may take place between two alcoholic olefins, between two carboxylic olefins, or between an alcoholic and a carboxylic olefin. As such, the monomer units will be arranged along the polyester chain in a random fashion. Hence, the polyester is referred to as a random polyester.

In a preferred embodiment of the invention, the diene ester monomer used in the preparation of the olefin-containing random polyester contains at least one terminal olefin group.

In a preferred embodiment of the invention, the diene ester monomer contains one terminal olefin group and one internal olefin group.

In a preferred embodiment of the invention, the diene ester contains two terminal olefin groups.

Particular diene ester monomers useful in the practice of the present invention may be represented by the following formula

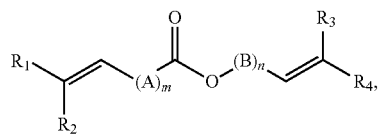

wherein

A and B, and m and n are as defined hereinabove, and the sum of n and m is an integer selected from 11, 12, 13 or 14;

$R_1$, $R_2$, $R_3$ and $R_6$, are independently residues representing H or $C_{1-10}$ alkyl, provided that only one of $R_1$, $R_2$, $R_3$ and $R_4$ residues can be $C_{1-10}$ alkyl, the remaining residues all being H.

In a particular embodiment, at least one of $R_1$ and $R_2$ or at least one of $R_3$ and $R_4$ represents $C_{1-10}$ alkyl.

Particular diene ester monomers include, but are not limited to compounds having the following formulae (a) through (g) below:

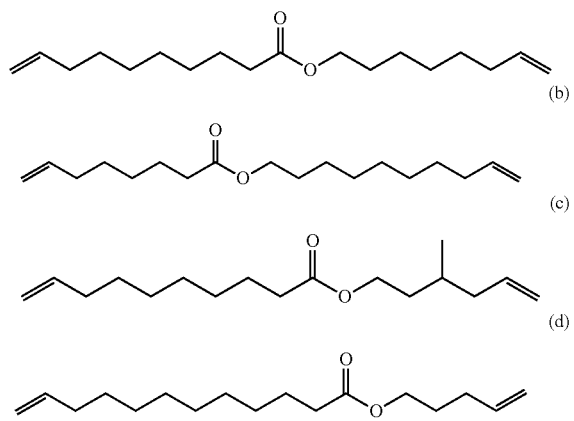

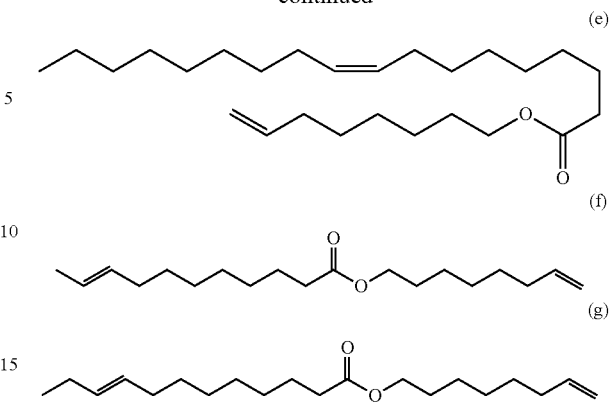

The diene ester monomers of formulae a), c), d), e), f) and g) are believed to be novel compounds. Hence, each of these compounds, their use in the preparation of olefin-containing random polyesters, as well as the random polyesters formed from said monomers, form independent aspects of the present invention.

The diene esters may be prepared by techniques well known in the art, using commercially available starting materials. By way of example, octenyl decenoate (compound (a) above) may be prepared by the trans-esterification of oct-7 en-1-ol with an alkyl dec-9-enoate in the presence of an acid, for example a strong acid, such as sulphuric acid. Reaction conditions are well known to a person skilled in the art and it is unnecessary to discuss them in further detail herein.

Diene ester polymerization to form the olefin-containing random polyester may be carried out by a diene metathesis reaction using a suitable metathesis catalyst.

Metathesis reaction conditions required to conjoin two olefin functional groups of reacting monomers are generally well known in the art. The reaction may proceed at room temperature, at elevated temperature or at low temperature. Typically, the reaction may be carried out at a temperature within the range of 0 to 120° C., more particularly 0 to 60° C., more particularly still about 50° C. Preferably, the reaction is carried out at a temperature such that the polymerization reaction proceeds rapidly and without substantial concomitant decomposition reactions, and the viscosity of the reaction mixture is such that typical industrial operations, such as mixing, pumping and stirring, should be easy to carry out. It is within the purview of the skilled addressee to select an appropriate reaction temperature taking these considerations into account.

The metathesis polymerization reaction may be carried out neat or in a solvent. If a solvent is to be employed, it should be unreactive with the catalyst. Suitable solvents may include those chlorinated or aromatic solvents, such as toluene, which are acceptable for use in an industrial process. Suitable solvents include, but are not limited to, docosane and tetraethylene glycol dimethyl ether. Alternatively, other solvents with a boiling point around or above that of the desired macrocyclic product can additionally be added to maintain liquidity of the mixture during the reaction, for example paraffin waxes, long chain esters such as phthalates, for example dialkyl phthalates, ethers, etc.

Owing to the reactivity of metathesis catalysts, the reaction should be carried out preferably in an inert atmosphere that is free of moisture and oxygen, or at least substantially so.

Furthermore, any material that will come into contact with a metathesis catalyst should be purified. Accordingly, in a process according to the present invention, it is desirable that the diene ester, as well as any solvents or other reagents employed in the metathesis reaction, are purified before the introduction of the catalyst. Purification entails the removal of contaminants that could otherwise negatively impact the reactivity of the metathesis catalyst. Such impurities would include water, alcohols, aldehydes, peroxides, hydroperoxides, protic materials, polar materials, Lewis base catalyst poisons, or any mixtures thereof. Methods of purifying metathesis catalysts are described in US 2014/0275595 and WO 2015/136093, for instance, which are herewith incorporated by reference.

Catalysts for effecting metathesis reactions are well known in the art. Generally, olefin metathesis catalysts are organometallic catalysts bearing a transition metal atom, such as vanadium, rhenium, titanium, tantalum, ruthenium, molybdenum or tungsten. Whilst varying considerably in terms of the ligands bound to the metal atom, all of the effective catalyst systems share the basic metal alkylidene or alkylidyne ligand structure. Reviews of metathesis catalysts useful in the present invention are described in Michrowska et al., Pure Appl. Chem., vol 80, No, 1, pp 31-43 2008; Schrock et al., Chem. Rev. 2009, 109, 3211-3226; and Grubbs et al., J. Am. Chem. Soc. 2011, 133, 7490-7496. Suitable catalysts are also described in the patent literature, for example in US 2013/0281706 and U.S. Pat. No. 6,306,988.

The variety of substituents or ligands that can be employed in the catalysts means that there are, today, a wide variety of catalysts available. Ligands or substituents may be selected to affect catalyst stability (to contaminants or temperature) or selectivity (chemo-, regio- and enantio-selectivity), as well as Turn Over Number (TON), and Turn Over Frequency (TOF). As is well known in the art, the TON describes the degree of activity of a catalyst, i.e. the average number of substrate molecules converted per molecule of catalyst, whereas TOF is a representation of catalyst efficiency {in units $h^{-1}$}.

Particularly useful catalysts in the metathesis reaction of the present invention are those metal alkylidene catalysts wherein the metal atom is either a Ruthenium, Molybdenum or Tungsten atom. Most preferred are said catalysts wherein the metal atom is Molybdenum or Tungsten.

Preferred Molybdenum or Tungsten catalysts are represented by the general formula

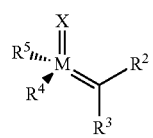

wherein

M=Mo or W;

X is O, or N—$R^1$; wherein $R^1$ is aryl, heteroaryl, alkyl, or heteroalkyl, optionally substituted;

$R^2$ and $R^3$ can be the same or different and are hydrogen, alkyl, alkenyl, heteroalkyl, heteroalkenyl, aryl, heteroaryl or alkoxy, which are optionally substituted;

$R^5$ is alkyl, alkoxy, heteroalkyl, aryl, aryloxy, heteroaryl, silylalkyl, silyloxy, optionally substituted;

and $R^4$ is a residue $R^6$—$X'$—, wherein $X'$=O and $R^6$ is aryl or heteroaryl, which are optionally substituted; or $X'$=S and $R^5$ is aryl or heteroaryl, which are optionally substituted; or $X'$=O and $R^6$ is ($R^7$, $R^8$, $R^9$)Si; wherein $R^2$, $R^8$, $R^9$ are alkyl or phenyl, which are optionally substituted; or $X'$=O and $R_6$ is ($R^{10}$, $R_{11}$, $R_{12}$)C, wherein $R^{10}$, $R^{11}$, $R^{12}$ are independently selected from phenyl, alkyl; which are optionally substituted;

or $R^4$ and $R^5$ are linked together and are bound to M via oxygen, respectively.

Particularly preferred catalysts are [2,6-Bis(1-methylethyl)benzenaminato(2-)](6'-bromo-4',5'-diphenyl[1,1':2', 1"-terphenyl]-3'-olato-κO)(2,5-dimthyl-1H-pyrrol-1-yl)(2-methyl-2-phenylpropylidene)-molybdenum; and (C-Bromo-4',5'-diphenyl[1,1':2',1"-terphenyl]-3'-olato)[2,6-dichloro-benzenaminato(2-)-ηN(2-)-ηN](2,5-dimethyl-1H-pyrrol-1-yl)(2-methyl-2-phenylpropylidene)-tungsten.

In general, the cyclo-depolymerization using metathesis may be performed using homogeneous or heterogeneous catalysts. Suitable homogeneous catalysts are disclosed in EP 2 703 081, WO 2014/139679, and US 2012/0302710, for instance. Suitable heterogeneous catalysts are disclosed in WO 2015/003815, WO 2015/003814, and WO 2015/049047, for instance. The disclosure of these publications in this respect is herewith incorporated by reference.

Particularly preferred catalysts include, but are not limited to:

Molybdenum catalyst A of the following formula:

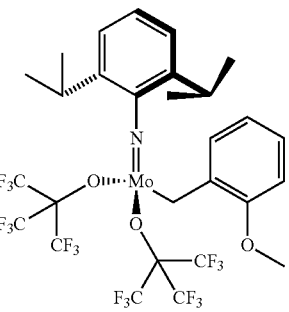

Molybdenum catalyst B (CAS: 1445990-85-1 sf the following formula:

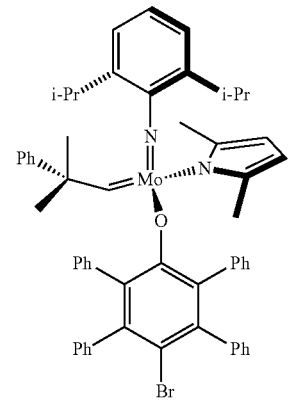

Ruthenium Catalyst C (CAS: 934538-04-2) of the following formula:

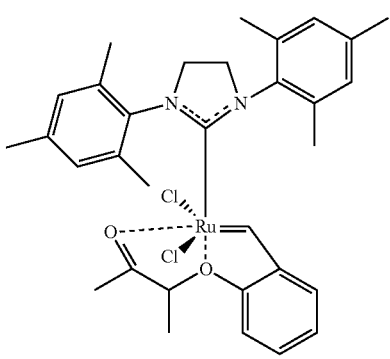

Of these, especially catalyst A has a very high thermal stability and is thus preferred.

The level of catalyst employed in the polymerization reaction described herein above may be from 10 to 1000 ppm, and more particularly, 50 to 200 ppm, and more particularly still 100 to 200 ppm on a molar basis.

The catalyst may be provided on a solid support. Suitable solid catalyst supports are well known in the art and include silica or alumina, or polymers, which are optionally end-capped to reduce the number of free hydroxyl groups. End-capping may be carried out by thermal treatment, and optionally using an end-capping reagent, such as a silylating reagent. Catalyst loading on the support may vary depending upon the particular synthetic transformation being carried out, but the catalyst may be present on the solid support in an amount of 1 to 10% by weight based on the total weight of the of catalyst and support.

The olefin-containing random polyester formed according to a method described herein above is converted into a macrocyclic lactone having the general formula

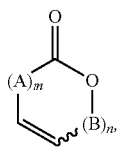

wherein A, B, m, and n are as defined above, by a process of cyclo-depolymerization.

The term "cyclo-depolymerization", as used herein, refers to a process whereby the polyester is depolymerized by bond scission of its ester or olefin functionality, followed by intramolecular cyclization of fragments formed by bond scission to form the desired macrocyclic lactone.

In a process of cyclo-depolymerization, the olefin-containing random polyester is cleaved either by scission of the olefin functionality or the ester functionality, depending upon the particular depolymerization chemistry employed. Bond scission is random, and a complex equilibrium mixture of cyclic and/or linear oligomers or polymers of different chain lengths will be formed. The smallest (and lowest boiling) fragment that will be obtained during cyclo-depolymerization is produced when contiguous ester functionalities or contiguous olefin functionalities react, and this cleaved fragment can undergo an intramolecular cyclization to form a desired macrocyclic lactone, which is subsequently removed from the reaction mixture by a suitable separation technique, such as distillation or filtration, such as membrane filtration, such as zeolite membrane filtration.

If the macrocyclic lactone is to be removed from the reaction mixture by distillation, the conditions of pressure and temperature should be such that, once the macrocyclic lactone is formed, it boils and is separated from the reaction mixture. Removing the macrocyclic lactone in this way will cause the reaction mixture to re-equilibrate and promote the formation of more macrocyclic lactone. The skilled person will understand that the removal of macrocyclic lactone by other means, such as membrane filtration, will likewise cause the reaction mixture to re-equilibrate and promote macrocyclic lactone formation.

In a particular embodiment of the present invention, cyclo-depolymerization is carried out by cleaving ester functionality by a process of trans-esterification.

Trans-esterification chemistry is well known in the art. Typical reaction conditions are described by Collaud et al. in U.S. Pat. No. 2,234,551. Cyclo-depolymerization by trans-esterification may be carried out by heating the olefin-containing random polyester in the presence of a trans-esterification catalyst. Suitable catalysts include, but are not limited to Lewis acids, and Brønsted acids and bases. Particularly preferred are the titanium tetra-alkoxides catalysts.

If the means of removing the macrocyclic lactone is distillation, then the reaction should be carried out at a temperature and pressure sufficient to distil off the macrocyclic lactone once it is formed. Once the macrocyclic lactone formed in this way is removed from the reaction vessel, any homo-dimer residues remaining can be recycled if desired.

A suitable temperature at which to carry out the reaction will depend upon the pressure in the reaction vessel. The reaction may be carried out under a reduced pressure that can be achieved economically on an industrial scale, for example in the range of 0.1 to 100 mbar. The temperature at which the reaction is carried out may be in the range of about 50 to 250° C., and more particularly 100 to 200° C.

In another preferred embodiment of the invention, cyclo-depolymerization is carried out by cleaving the olefin functionality by olefin metathesis, as heretofore described.

Depending upon the olefin functionality that is cleaved, all manner of oligomeric or polymeric fragments can be formed. However, when contiguous olefin functionalities react, the fragments formed can cyclize to form the desired macrocyclic lactone. Removal of this macrocyclic lactone from the reaction mixture by distillation or by other means described above will drive the reaction to produce more macrocyclic musk, which in principle can result in substantially 100% conversion of the polyester to the desired macrocyclic lactone.

The skilled person may select the reaction conditions (for example, temperature and pressure) based on a number of considerations including the activity of the particular catalyst employed; the desire to promote cyclo-depolymerization and reduce unwanted reactions, such as double bond isomerization; and the desire for the reaction mixture to be a low viscosity liquid. Furthermore, when it is desired to effect the separation of the macrocyclic lactone by distillation, the temperature and pressure should be selected such that the lactone can distil, preferably without carrying over in co-distillates.

Typically, the reaction may be run at atmospheric pressure or at reduced pressure, for example in the range of 1 bar to 1 mbar, more particularly 10 to 100 mbar, and more particularly still 10 to 30 mbar. Typical temperatures may be between ambient temperature and 250° C., more particularly 100 and 250° C., and more particularly still 150 to 200° C.

Any of the metathesis catalysts referred to herein above may be used in the cyclo-depolymerization reaction. However, tungsten and molybdenum metathesis catalysts may be particularly useful if it is desirable to reduce any side reactions that might occur, such as double-bond isomerization reactions.

Given that the separation of the macrocyclic lactone from the reaction mixture is essential to re-equilibrate the mixture and promote further macrocyclic lactone formation, it might be necessary to heat the mixture in order to distil off the lactone. If heat is applied to the reaction mixture, it is desirable to employ metathesis catalysts that are thermally stable at the distillation temperature. Of course, if the macrocyclic lactone is separated by membrane filtration rather than by distillation, then this precaution might not be necessary.

Irrespective of any consideration regarding the thermal stability of any given catalyst, the cyclo-depolymerization reaction may be carried out under conditions whereby the catalyst is physically separated from the reaction mixture that is heated to the distillation temperature of the macrocyclic lactone.

For example, the catalyst may be contained in a first part of a reactor at a first temperature that is below the distillation temperature of the macrocyclic lactone, and at which temperature the catalyst is stable, or substantially so. The first part of the reactor is in fluid communication with a second part of the reactor at a second temperature that is at or above the temperature at which the macrocyclic lactone distils. The reactor is equipped with means for distilling the macrocyclic lactone, such that when the reaction mixture flows from the first part of the reactor to the second part of the reactor, the macrocyclic lactone is separated from the reaction mixture by distillation. The means for distilling the macrocyclic lactone may consist of a conventional distillation vessel and column, or it may consist of an apparatus for molecular distillation (such as wiped-film distillation apparatus). The reaction mixture may be in continuous circulation between first and second parts of the reactor, whereupon it is heated and cooled as it passes between second and first parts of the reactor.

The processes described hereinabove are useful in the preparation of all manner of macrocyclic lactones. Preferred macrocyclic lactones are those that are useful in perfumery. Particularly preferred macrocyclic lactones are those containing 14 to 17 carbon atoms in the ring.

Examples of preferred macrocyclic lactones include, but are not limited to, AMBRETTOLIDE™ (both qualities with the double bond in the 9-position or the 7-position) NIRVANOLIDE™, HABANOLIDE™ or GLOBALIDE™. These macrocyclic musk compounds contain an unsaturation in the ring, and as such can exist in E/Z form. The present invention is concerned with processes of making these macrocyclic musks in pure E or pure Z form, or the E/Z mixtures in any ratio.

In addition to these musks, their saturated equivalents can also be produced by hydrogenation of the carbon-carbon double bond in a manner known per se. These hydrogenated derivatives include, but are not limited to, hexadecanolide and cyclopentadecanolide.

Whereas the musks are referred to by their trade names, the skilled person will appreciate that this is intended for ease of reference only, and the applicant intends that the teaching of the invention applies to the preparation of the generic musk molecules. For each of the musks referred to by their trade names above, the skilled person would either be familiar with the more conventional chemical nomenclature for naming the musks, or would realize that one can find the correspondence between trivial name and chemical nomenclature in standard perfumery reference works, such as Leffingwell, or thegoodsceritcompany.com websites.

The present invention is further illustrated by the following non-limiting examples:

Example 1: Preparation of Octenyl Decenoate

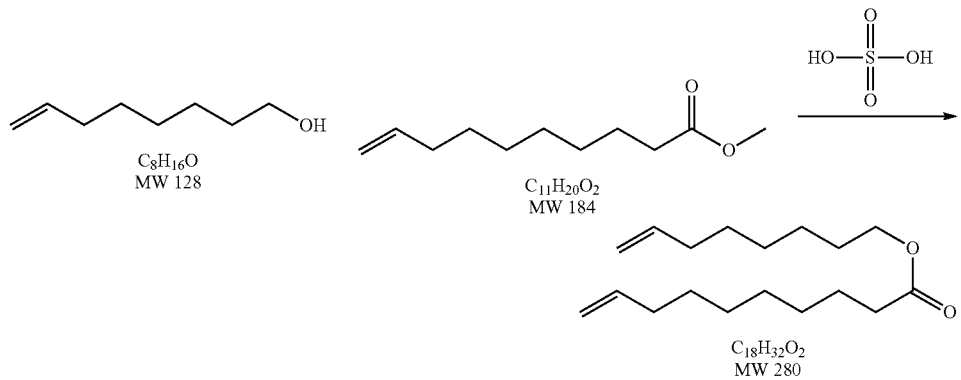

To a 2 L sulfonation flask, equipped with thermometer, still head, condenser, and receiver and connected to the house vacuum via a cold trap was added methyl 9-decenoate (500 g, 2.70 mol), 7-octenol (350 g, 2.70 mol, 1.01 eq) and, with stirring, concentrated sulfuric acid (10 g, 2%).

Vacuum was applied and kept at 28 mbar. The mixture was then heated to 100° C. Distillation started at about 75° C.

Reaction Log:

| Time | Temperature of the reaction mixture (PT) | Temperature of the still head (HT) | Pressure (P) |
|---|---|---|---|
| 10:30 | Start of heating | | |
| 11:00 | 85° C. | 55° C. | 28 mbar |
| 11:22 | 90° C. | 53° C. | 28 mbar |
| 11:58 | 98° C. | 36° C. | 19 mbar |
| 13:47 | 98° C. | 26° C. | 19 mbar |

-continued

| Time | Temperature of the reaction mixture (PT) | Temperature of the still head (HT) | Pressure (P) |
|---|---|---|---|
| 15:07 | 100° C. | 26° C. | 18 mbar |
| 17:22 | 100° C. | 27° C. | 18 mbar |
|  | —> Heat turned off |  |  |

Distillate + cold trap = 91.75 g

After the reaction mixture was cooled to room temperature, saturated sodium bicarbonate solution (50 ml) was added and stirred for 15 min. The mixture was poured to a separating funnel to permit the layers to settle. The aqueous layer was separated and the organic layer was washed with water (2×200 ml), dried with magnesium sulphate and filtered.

737.7 g crude product was obtained.

Tocopherol (0.2 g) was added to the mixture and it was then purified by distillation through a 0.5 m Sulzer packed column.

Preparation of Octenyl Decenoate was confirmed by GLC analysis performed on an HP6890 using a 25 m HP5 (0.33 m) column programmed at 70° C. to 220° C. at 15° C./min.

Example 2: Preparation of Poly Octenyl Decenoate

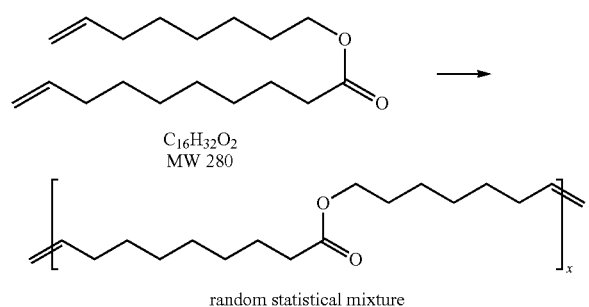

$C_{16}H_{32}O_2$
MW 280 random statistical mixture

A 1 L glass jacketed autoclave (Buchi) was fitted with an anchor stirrer, baffle, temperature probe, argon gas inlet, vacuum line and liquid addition line. This latter was a simple ball valve fitted with a septum inlet. When liquids were added, they were added to the reactor through a stainless steel cannula under positive argon pressure. The cannula was withdrawn above the valve and the valve closed before the cannula was extracted. Before use, the glass body of the reactor was heated to 130° C. for 3 h and allowed to cool overnight under vacuum.

Stock solutions and feed were prepared in a glove box under dry nitrogen (five 0s grade). They were placed in sealed Schlenk tubes and removed from the glove box.

Reaction and material transfers were done under argon, but it is anticipated this could readily be replaced by five 0s grade dry nitrogen.

The reactor was rated to 12 bar, but was fitted with a 6 bar bursting disk with a vent line to the back of the fume hood.

Stock Solutions:

To assist ease of handling on small laboratory scale, stock solutions of triethyl aluminum (25% in toluene, as received) and [2,6-Bis(1-methylethyl)benzenaminato(2-)](6'-bromo-4',5'-diphenyl[1,1':2',1''-terphenyl]-3'-olato-κO)(2,5-dimethyl-1H-pyrrol-1-yl)(2-methyl-2-phenylpropylidene)-molybdenum metathesis catalyst (Molybdenum catalyst B; 0.021 Min d6-benzene for ease of NMR analysis) were used.

Feed Pre-Treatment:

Oct-7-enyl dec-9-enoate ($H_2O$ 53 ppm, Peroxide Value PV 1.6 meq/kg) was charged to the argon filled reactor through a cannula. Adding via a funnel and purging was less effective (only ~50% conversion observed).

To the oct-7-enyl dec-9-enoate under a slight positive pressure of five 0s grade nitrogen (1.3 bar), was added triethyl aluminum (1 mol %) as a stock solution in toluene at room temperature (ca. 25° C.). The cannula was flushed with dry toluene (2 ml) before being removed, as triethyl aluminum is pyrophoric at >10% concentration. The mixture was stirred for 3 h at room temperature. It appears that heating the mixture to 50° C. or more at this stage is detrimental to the conversion. The reactor was taken through a vacuum (7 mbar)/argon (1.3 bar) purge cycle three times to remove any impurity build-up.

Polymerisation:

To the pre-treated oct-7-enyl dec-9-enoate was added a solution of 200 ppm Molybdenum catalyst B. After about 15 min, the viscosity increased and the reactor was heated to 50° C. to maintain the reaction as a liquid. This took around 15 min. The reaction was not exothermic. Note that the reaction was less effective if the addition of Molybdenum catalyst B was carried out at 50° C. from the beginning.

Following feed pre-treatment as described above:

| Time | Internal temperature (IT) | Pressure measured in pump line (P) | Comments |
|---|---|---|---|
| 13:30 | 23° C. | Full vacuum applied | Catalyst addition |
| 13:40 | 19° C. | 50 mbar | Degassing |
| 13:45 | 19° C. | 40 mbar | Hazy appearance; heating started |
| 14:00 | 45° C. (bath: 50° C.) | 35 mbar | Strong degassing; volume increased |
| 14:10 | 50° C. | 18 mbar | Gas evolution slowly decreasing |
| 14:30 | 51° C. | 12 mbar | Volume decreased |
| 15:00 | 51-52° C. (bath: 50-51° C.) | 12 mbar | Less gas, mixture more viscous |
| 15:30 | 52° C. | 12 mbar | Still full vacuum; reaction mixture significantly more viscous |
| 16:00 |  |  | Heating and stirring stopped |

The reaction mixture cooled overnight and solidified. It was melted out (jacket at 50° C.) and sampled for NMR and GPC (see below) yielding 238 g. Additional material was washed from the reactor and overheads with toluene, which was removed under vacuum to yield an additional 37 Total: 275 g. The theoretical maximum at 100% conversion of pure material is 270 g. The crude polymer contains residual catalyst and aluminates.

Formation of the polymer was confirmed using Gel Permeation Chromatography (GPC) analysis. Analysis was performed on a self-built GPC. Two columns were used in series with a guard column (Phenogel 5 mm 100 Å followed by Phenogel 5 mm, 1000 Å, both obtained from Phenomenex), eluting with TF-IF and using a refractive index detector.

Example 3: Preparation of Ambrettolide by Cyclo-Depolymerization Using Trans-Esterification

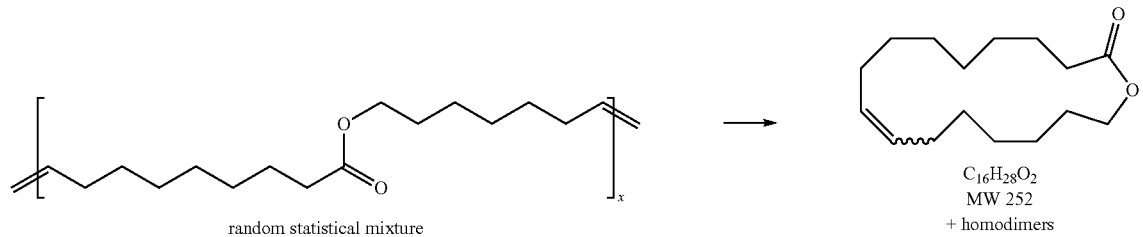

random statistical mixture

A round-bottomed flask fitted with Claisen head, magnetic stirrer and thermometer was attached to a peristaltic pump to allow addition of polyethylene glycol (PEG200) during the reaction.

The flask was charged with polymer (100 g, which may be handled as a liquid at 50° C.). PEG200 (130 g) was added together with titanium tetra-iso-propoxide (5 g, 17 mmol). Initially, the mixture was immiscible. The vacuum was set to 10 mbar and the stirred mixture was heated. Degassing was observed when the mixture reached about 40-50° C. The vacuum was temporarily reduced to 30-50 mbar and then warmed up slowly. When the mixture reached 110-120° C., degassing occurred and the mixture became viscous, with the polymer starting to dissolve in PEG. At 160° C., the mixture became less viscous and easily stirrable again. Heating was continued to a reaction temperature of 190-200° C.

As material started to distil out with a head temperature of ca. 170° C. at 10 mbar, PEG was pumped into the flask to maintain a standard liquid level (total added: 885 g).

A total distillation time of ca. 40 h was used over five working days. Analysis of the fractions for E- and Z-Ambrettolide was carried out by relative peak area GLC. Fractions were combined and then worked up:

To the combined fractions (707 g) was added water (700 ml), which was extracted with hexane (700 ml). Three phases were observed. The middle one was treated with the water phase by extracting with hexane (2×200 ml). The combined organics were washed twice with water (2×200 ml). The organic layers were combined, dried over magnesium sulphate, filtered and solvent removed on the rotary evaporator to give crude Ambrettolide (43.0 g, 171 mmol). GLC showed a purity of 87% by rpa. This represents a chemical yield of 75%.

Example 4: Preparation of Ambrettolide by Cyclo-Depolymerization Using Metathesis and Distillation The present reaction was carried out in a glove-box containing a dry, low oxygen atmosphere (nitrogen or argon) for ease of handling.

Polyoctenyl decenoate (prepared as described above; 0.25 g) was placed in a Kugelrohr bulb. Molybdenum catalyst A (see above) was added as a solution in toluene (250 mol·ppm) and the system placed under vacuum (0.2 mbar). After removal of the toluene, the Kugelrohr oven was heated to 130-150° C. and Ambrettolide was distilled out. When the rate of distillation of Ambrettolide slowed, a further aliquot of catalyst was added and the distillation continued. Repetition of this technique could achieve yields of over 60% Ambrettolide from the polymer.

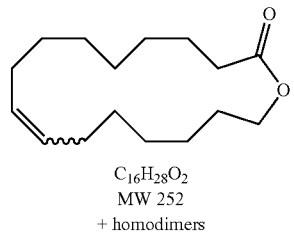

$C_{16}H_{28}O_2$
MW 252
+ homodimers

Example 5: Preparation of Ambrettolide by Cyclo-Depolymerization Using Metathesis and Distillation The present reaction was carried out in a glove-box containing a dry, low oxygen atmosphere (nitrogen or argon) for ease of handling.

Polyoctenyl decenoate (prepared as described above; 0.25 g) was dissolved in docosane (2.5 ml) and placed in a Kugelrohr bulb. Molybdenum catalyst A (see above) was added (400 mol·ppm) and the system placed under vacuum (0.5 mbar). The Kugelrohr oven was heated to 130-150° C. and a mixture of Ambrettolide and docosane distilled out. Periodically, fresh aliquots of catalyst and solvent were added and the distillation continued to yield more Ambrettolide.

Example 6: Preparation of Ambrettolide by Cyclo-Depolymerization Using Metathesis The present reaction was carried out in a glove-box containing a dry, low oxygen atmosphere (nitrogen or argon) for ease of handling.

Polyoctenyl decenoate (prepared as described above; 0.25 g) was dissolved in tetraethylene glycol dimethyl ether. Molybdenum catalyst A (see above; 400 ppm) was added and the mixture heated to 160° C. for 6 h. Internal standard glc, analysis showed 13.8% Ambrettolide formed.

Example 7: Preparation of Ambrettolide by Cyclo-Depolymerization Using Metathesis and Filtration Polyoctenyl decenoate (prepared as described above; 50 g) was added to ethyl acetate (700 ml) and dissolved at 60° C. Flux measurements through a 1 nm C8 modified $TiO_2$ membrane were carried out at a trans-membrane pressure of 5 bar. Ruthenium catalyst C (see above; 0.6 mol %) was added. The unit was placed under pressure (5 bar). Constant volume diafiltration was performed with ethyl acetate for approx. 2 hours. The permeate and retentate were analysed and shown to contain Ambrettolide (20% overall yield). This reaction can be continued to produce and separate more Ambrettolide.

The invention claimed is:
1. A process for preparing and isolating a macrocyclic lactone by the cyclo-depolymerization of an olefin-containing random polyester contained in a reaction mixture, the process comprising the steps of:

i) depolymerizing the olefin-containing random polyester in a reaction mixture to form fragments capable of intramolecular cyclization;
ii) intramolecular cyclization of said fragments to form a desired macrocyclic lactone; and
iii) concomitant separation of the macrocyclic lactone from the reaction mixture,
wherein the olefin-containing polyester contains at least one unit of the formula

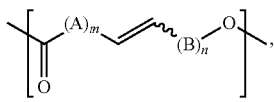

wherein
A is a divalent radical —CHR—, wherein R is hydrogen or a $C_{1-4}$ alkyl group;
B is a divalent radical —CHR'—, wherein R' is hydrogen or a $C_{1-4}$ alkyl group;
the sum of n and m is an integer selected from 11, 12, 13 or 14; and
wherein the divalent radicals A and B in the unit may be the same or different.

2. The process according to claim 1 wherein the olefin-containing polyester contains at least one each of the following units

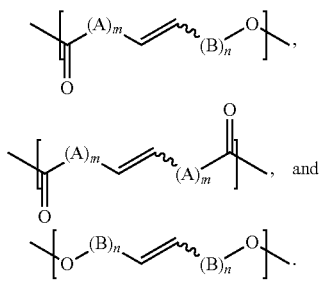

3. The process according to claim 1, wherein the polyester contains at least 5 to 50 units.

4. The process according to claim 1, wherein the cyclo-depolymerization reaction is effected by trans-esterification or metathesis.

5. The process according to claim 4, wherein the metathesis reaction is catalysed with a catalyst selected from the general formula

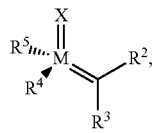

wherein
M=Mo or W;
X is O, or N—$R^1$, wherein $R^1$ is aryl, heteroaryl, alkyl, or heteroalkyl, optionally substituted;
$R^2$ and $R^3$ can be the same or different and are hydrogen, alkyl, alkenyl, heteroalkyl, heteroalkenyl, aryl, heteroaryl or alkoxy, which are optionally substituted;
$R^5$ is alkyl, alkoxy, heteroalkyl, aryl, aryloxy, heteroaryl, silylalkyl, silyloxy, optionally substituted; and $R^4$ is a residue $R^6$—X'—, wherein X'=O and $R^6$ is aryl or heteroaryl, which are optionally substituted; or X'=S and $R^6$ is aryl or heteroaryl, which are optionally substituted;
or X'=O and $R^6$ is ($R^7$, $R^8$, $R^9$)Si; wherein $R^7$, $R^8$, $R^9$ are alkyl or phenyl, which are optionally substituted; or X'=O and $R^6$ is ($R^{10}$, $R^{11}$, $R^{12}$)C, wherein $R^{10}$, $R^{11}$, $R^{12}$ are independently selected from phenyl, alkyl; which are optionally substituted;
or $R^4$ and $R^5$ are linked together and are bound to M via oxygen, respectively.

6. The process according to claim 1, wherein the concomitant separation of the macrocyclic lactone from the reaction mixture is effected by distillation.

7. The process according to claim 1, wherein the macrocyclic lactone is selected from the group consisting of E/Z-17-oxacycloheptadec-7-en-1-one; E/Z-17-oxacycloheptadec-9-en-1-one; E/Z-13-methyloxacyclopentadec-10-en-2-one; and E/Z-1-oxacyclohexadec-12-en-2-one.

8. The process according to claim 7, wherein the macrocyclic lactone is hydrogenated to form the hydrogenated macrocyclic lactone corresponding to E/Z-17-oxacycloheptadec-7-en-1-one; E/Z-17-oxacycloheptadec-9-en-1-one; E/Z-13-methyloxacyclopentadec-10-en-2-one; or E/Z-1-oxacyclohexadec-12-en-2-one.

9. The process according to claim 1, wherein the polyester is prepared by acyclic diene metathesis polymerization of a diene-ester.

10. The process according to claim 9, wherein the diene-ester contains at least one terminal olefin group.

11. The process according to claim 9, wherein the diene-ester contains one terminal olefin group and one internal olefin group.

12. The process according to claim 9, wherein the diene-ester contains two terminal olefin groups.

13. The process according to claim 9, wherein the diene-ester has the following formula

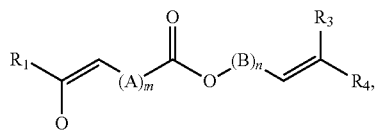

wherein
A is a divalent radical —CHR—, wherein R is hydrogen or a $C_{1-4}$ alkyl group;
B is a divalent radical —CHR'—, wherein R' is hydrogen or a $C_{1-4}$ alkyl group;
the sum of n and m is an integer selected from 11, 12, 13 or 14; and
wherein the divalent radicals A and B in the unit may be the same or different; and
$R_1$, $R_2$, $R_3$ and $R_4$, are residues representing H or $C_{1-10}$ alkyl, provided that only one of $R_1$, $R_2$, $R_3$ and $R_4$ residues can be $C_{1-10}$ alkyl, the remaining residues all being H.

14. The process according to claim 13, wherein the diene-ester is selected from the group consisting of (a)
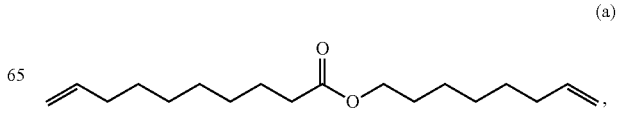

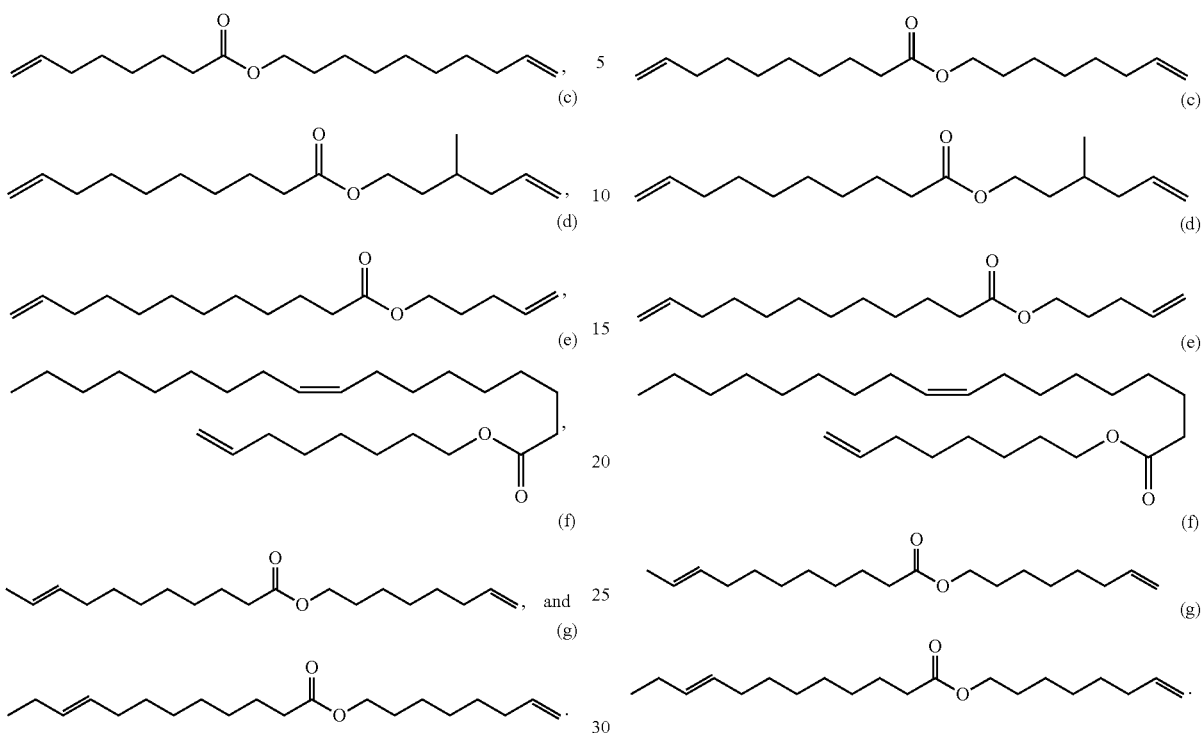
15. A diene-ester prepared by the process as defined in claim 14, selected from compounds (a), (c), (d), (e), (f) and (g).
16. A diene-ester selected from compounds (a), (c), (d), (e), (f) and (g),
17. The process according to claim 10, wherein the diene-ester contains one terminal olefin group and one internal olefin group.
18. The process according to claim 10, wherein the diene-ester contains two terminal olefin groups.
* * * * *

UNITED STATES PATENT AND TRADEMARK OFFICE
CERTIFICATE OF CORRECTION

PATENT NO.       : 10,633,359 B2
APPLICATION NO.  : 16/077187
DATED            : April 28, 2020
INVENTOR(S)      : Paul Nicholas Davey It is certified that error appears in the above-identified patent and that said Letters Patent is hereby corrected as shown below:

In the Claims

In Claim 13 at Column 16, Lines 39-44, the formula should read:

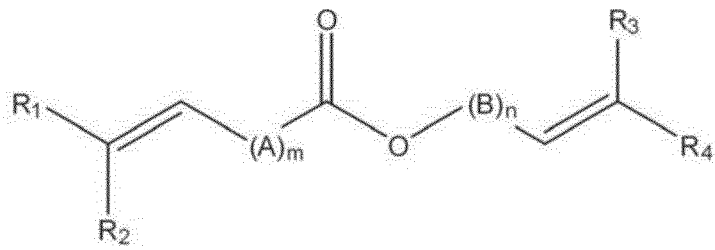

Signed and Sealed this
Fourth Day of August, 2020

Andrei Iancu
*Director of the United States Patent and Trademark Office*